United States Patent [19]

Abrams et al.

[11] Patent Number: 4,873,981
[45] Date of Patent: Oct. 17, 1989

[54] ELECTROCONVULSIVE THERAPY APPARATUS AND METHOD FOR AUTOMATIC MONITORING OF PATIENT SEIZURES

[75] Inventors: Richard Abrams, Chicago; Conrad M. Swartz, Lake Forest, both of Ill.

[73] Assignee: Somatics, Inc., Lake Bluff, Ill.

[21] Appl. No.: 258,209

[22] Filed: Oct. 14, 1988

[51] Int. Cl.[4] .............................................. A61N 1/36
[52] U.S. Cl. ................... 128/419 S; 128/731
[58] Field of Search ............... 128/419 S, 791, 731, 128/732

[56] References Cited

U.S. PATENT DOCUMENTS

| | | | |
|---|---|---|---|
| 3,623,477 | 11/1971 | Trent | 128/731 |
| 3,993,046 | 11/1976 | Fernadez et al. | 128/732 |
| 4,103,068 | 3/1977 | Settle et al. | 128/732 |
| 4,503,863 | 3/1985 | Katims | 128/732 |
| 4,709,700 | 12/1987 | Hyrman | 128/419 S |
| 4,744,029 | 5/1988 | Raviv et al. | 128/731 |

OTHER PUBLICATIONS

Fink, M. and Johnson, L.: Monitoring the Duration of Electroconvulsive Therapy Seizures, "Cuff" and EEG Methods Compared, Arch. Gen. Phychiatry, vol. 39, Oct. 1982, 1189–1191.

Liberson, W. T. (1945), Time Factors in Electric Convulsive Therapy, Yale J. Biol. Med., 17; 571–578.
Christensen, P. and Koldback, I. (1982), EEG Monitored ECT, Brit. J. Psychiat., 141; 19–23.
Valentine, M. et al. (1968), A Comparison of Techniques in Electroconvulsive Therapy, Brit. J. Psych., 11, 989–99.

Primary Examiner—Lee S. Cohen
Assistant Examiner—Scott M. Getzow
Attorney, Agent, or Firm—Eliot S. Gerber

[57] ABSTRACT

A method and system in electroconvulsive therapy (ECT) to automatically monitor and display the occurrence and the duration of the seizure activity generated during the administration of the electrically induced therapeutic seizures. The ECT device includes a special-purpose electroencephalograph (EEG) system to detect a specific EEG parameter (e.g. integrated voltage) of the electrically induced EEG seizure. The detected integrated voltage is converted to digital data and compared to a threshold reference value previously obtained from the same patient. The operator is informed by an electronic alphanumeric elapsed time display or indications on a moving strip chart paper record, or oscilloscope CRT screen, when the parameter has crossed the predetermined threshold reference value and how long since the termination of the ECT the parameter has taken to reach the reference value.

13 Claims, 1 Drawing Sheet

ELECTROCONVULSIVE THERAPY APPARATUS AND METHOD FOR AUTOMATIC MONITORING OF PATIENT SEIZURES

BACKGROUND OF THE INVENTION

1. Field of the Invention

The present invention relates to medical apparatus and more particularly to electroconvulsive therapy apparatus.

2. Description of the Related Art

Electroconvulsive therapy ("ECT"), sometimes called "shock therapy", is frequently used to treat major depression. A report of a NIMH panel (National Institute of Mental Health), reported in *Science* (June 28, 1985, pg. 1510, 1511), concluded that "not a single controlled study has shown another form of treatment to be superior to ECT in the short-term management of severe depressions." The *Science* article noted that the complication rate is about 1 in 1700 treatments and severe and prolonged memory loss is extremely rare, and possibly non-existent.

In electroconvulsive therapy (ECT) generally two electrodes are applied to the forehead of the patient, one on the left and the other on the right side. An electric current is applied between the two electrodes on the forehead. A small portion of the current reaches the brain, the rest being deflected by the skin and skull.

In the "Thymatron" ECT instrument (TM of Somatics, Inc., Lake Bluff, Illinois) the stimulus is a brief series of electrical square waves. The stimulus is a constant current of 0.9 amps limited to 450 volts, consisting of 140 bipolar pulses per second of 1 msec. width, which is adjustable 0.2–4.0 seconds in duration.

The physician determines the length of the applied electricity, taking into account such factors as the patient's age, size, physical condition and prior history of electroconvulsive therapy. The physician may, with presently available apparatus, reasonably accurately select the desired electrical duration.

The ECT therapy is based upon inducing an electrical response in the neural tissue of the patient's brain. This appears on an electroencephalograph (EEG) instrument, using analog printed wavy lines, as a pattern similar to a typical epileptic grand mal seizure pattern. It is believed that the therapeutic benefit of the ECT is primarily due to the induced seizure.

It has recently been recognized that when administering ECT it is important for the physician to monitor the brain's electrical activity to determine both the occurrence and the duration of the induced seizure (National Institutes of Health, Consensus Conference, Electroconvulsive Therapy, J.A.M.A. 254:2103–2108, 1985). An electrical stimulus that does not induce a seizure, or one that induces a seizure of insufficient duration (e.g., less than 25 seconds) is not considered to have any therapeutic effect. The treatment must be repeated with a larger electrical dosage, i.e. generally a greater electrical charge, to try to induce a seizure expected to be of full therapeutic benefit to the patient. On the other hand, a seizure that is too long (e.g., longer than 3 minutes) may cause excessive memory impairment in the patient, or require more intensive supervision of the patient during and after the treatment. It is customary medical practice to immediately terminate such prolonged seizures by administration of suitable anticonvulsant agents according to the physician's judgment.

The existing methods used to monitor the electrical activity of the brain during ECT are based on conventional EEG technology. Generally an EEG device is used to amplify the patient's brain waves, filter the amplified brain wave signals to remove muscle artifact and ambient electrical noise, display the brain wave activity in the form of wavy lines on paper or lines on an oscilloscope screen, or similarly fluctuating audible tones played through an audible speaker. The physician may then judge the occurrence of the seizure by interpreting the paper EEG record, oscilloscope display, or auditory EEG signal. He then makes a determination of the length of the seizure by further interpreting the particular representation of the EEG signal, thereby a spike-like form on an EEG graph, while simultaneously viewing a timepiece. However, judgments based on interpretations of the visual, or auditory, EEG signals require special medical expertis and familiarity with EEG patterns that typically occur during ECT. Such judgments are necessarily subjective, rely on the attention and experience of the physician, and have been reported in the medical literature to be unreliable (Ries, R.K., Biol. Psychiat. 20:94–119, 1985). Moreover, to determine the duration of the seizure, the physician must attend to the visual, or auditory, representation of the EEG signal, as well as to a separate timepiece, just when his attention is urgently required to observe the patient undergoing the seizure.

SUMMARY OF THE INVENTION

A method and system in electroconvulsive therapy (ECT) automatically monitors and displays the occurrence and duration of an electrically-induced therapeutic seizure. The patient's brainwave electrical activity is monitored by electroencephalograph (EEG) to determine the voltage level during induced seizure. The operator is informed, by an elapsed-time electronic alphanumeric display or indicators on a moving paper strip chart record or an oscilloscopic (CRT) display that the voltage level has fallen to a predetermined reference value. The voltage reference level is chosen to discriminate between seizure and non-seizure activity. The display also shows how long it took from the start of the seizure to reach the reference level. The reference level is predetermined and chosen as an artificial end-of-seizure point.

OBJECTIVES AND FEATURES OF THE INVENTION

It is an objective of the present invention to provide a method and system in electroconvulsive therapy ECT in which the ECT device automatically will determine the termination and duration of the induced seizure and will automatically display that information to the physician.

It is a further objective of the present invention to provide such an ECT method and system in which the physician need not be distracted from watching the patient in order to time the ECT induced seizure.

It is a further objective of the present invention to provide such an ECT method and system in which an objective and automatic record may be obtained of the termination and duration of the induced seizure without requiring the expertise and attention of a physician in viewing the wavy lines of an EEG.

It is a feature of the present invention to provide a method and system for electroconvulsive therapy ECT to monitor the termination of an induced seizure in a patient. The system includes an ECT device having generally two electrodes removably securable on the head of the patient and means for applying electricity through the electrodes in an electroconvulsive therapy session to induce seizure.

A special-purpose electroencephalograph EEG means to detect electrical brain waves of the patient is preferably built into an electrically integrated system with the ECT device. The EEG includes amplifying means to amplify the brain waves and generally two electrodes adapted to be removably secured to the head of the patient; system memory means establishing and storing-in system memory a baseline reference of a brain wave parameter (for example, integrated voltage over 1 second), timer means to commence monitoring of brain waves for the termination of the seizure in the range of 1–30 seconds after ceasing the said application to induce seizure, measurement means for automatically measuring the termination of seizure as determined by the decline of the monitored brain wave parameter to the said established reference, and display means for displaying said termination.

Further features of the invention are that the system includes elapsed time means for measuring the time from the commencement of monitoring until the established reference is reached and display means for displaying said elapsed time. In addition, preferably the system includes means for determining and displaying the lack of a seizure by failure to reach the established reference within a selected time period.

BRIEF DESCRIPTION OF THE DRAWINGS

Other objectives and features of the present invention will be apparent from the following detailed description of a preferred embodiment thereof, taken in conjunction with the accompanying drawings.

In the drawings.

DESCRIPTION OF THE PREFERRED EMBODIMENT

The apparatus and method of the present invention employ the setting of criteria, by the physician, for electronic processing of a selected EEG parameter in order to determine the occurrence and duration of the ECT electrically induces seizure. Preferably, and in the below-described embodiment, the parameter of EEG voltage level is used for illustrative purposes; however, other computed EEG parameters (e.g., means peak voltage, coherence, total power) can also be validly employed in this invention.

Figure 1:
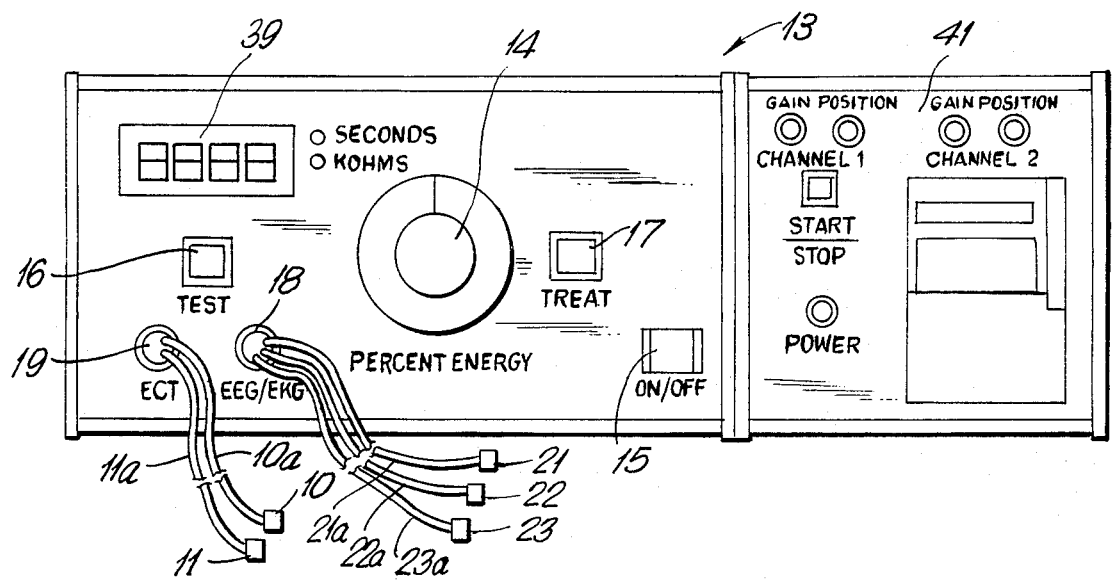
FIG. 1 is a front plan view of the ECT-EEG device of the present invention.

As shown in FIG. 1, the patient is readied for an electro-convulsive therapy ECT session by applying two electrodes 10, 11 to the head of the patient. The ECT apparatus 13 applies electricity through electrodes 10, 11 to induce a therapeutic brain seizure. The electrodes 10, 11 are connected by leads 10a, 11a to the ECT plug connector 19 of the ECT apparatus 13. The EEG electrode leads 21a–23a are connected through connection plug 18. The physician will push the on/off power button 15, select the duration of the ECT using the timer dial 14, push the test button 16 to test the electrode impedance which is displayed on LED alphanumeric display 39 and will push and hold treatment button 17 to apply the ECT charge. A suitable ECT apparatus is the "Thymatron" (TM of Somatics, Inc., Lake Bluff, Illinois).

The patient's electrical brain wave activity is monitored by a special purpose electroencephalographic EEG device 20. The EEG device 20 is not the conventional type of EEG device in which the brain waves appear as wavy lines on a strip chart or CRT oscilloscope. Instead, it is a special purpose EEG device whose function is to alert the physician during the ECT therapy session of the termination of a seizure or whether a seizure has, in fact, occurred, as a result of the applied electricity.

Figure 2:
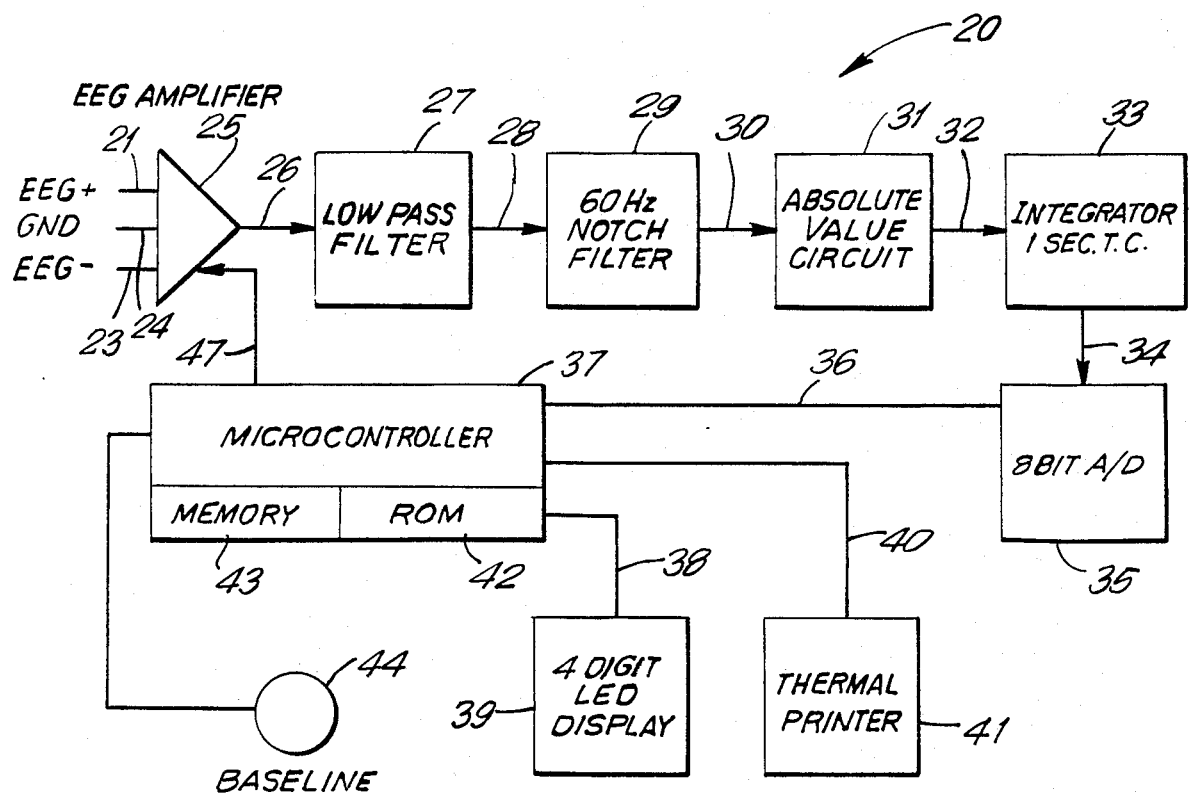
FIG. 2 is a block diagram of the EEG device of the present invention.

As shown in FIG. 2, the EEG device 20 of the present invention includes three conductive electrodes 21–23 which are removably secured to the skin of the patient. Preferably electrode 21 is applied on the patient's left forehead as a positive lead, electrode 22 is applied as a ground to the patient's left shoulder, and electrode 23 is applied to the patient's right forehead as a negative lead. The electrodes are electrically connected to the high-gain low-noise EEG amplifier 25 by leads 22a–23a which are connected through the plug connector 18. Amplifier 25 amplifies brain waves 10,000 times.

The amplified analog brain waves are conducted on line 26 to the low band pass filter 27 which eliminates low frequencies and passes only higher frequencies. The setting of filter 27 is in the 2.5–25 HZ range, and preferably is 25 HZ. The amplified brain waves are then passed through a notch filter 29 set at 60 HZ to eliminate ambient electrical noise, which generally is at 60 HZ (in the United States). The amplified brain waves are then conducted on line 30 to absolute value circuit 31. The absolute value circuit will, in effect, invert the negative wave portion and treat it as a positive value, so that both positive wave segments and negative wave segments are added together as positive waves. Its resulting analog signal is sent, on line 32, to integrator 33. The time period of the integrator is pre-set, in the range 0.5–3 seconds and is preferably 1 second. It integrates the voltage in the patient's brain wave over the selected one-second period.

Alternatively, as mentioned above, a different parameter than integrated voltage over a selected short interval of time, may be selected. For example, the selected parameter may be mean peak amplitude during a selected period, for example, 2 seconds.

The output of integrator 33 is sent, on line 34, to A/D converter 35 (analog-to-digital converter) which preferably is an 8-bit A/D converter operating at a rate of at least 200 samples per second.

The digital output of A/D converter 35 is sent, over line 36, to microcontroller 37. The microcontroller 37 is a solid-state large-scale integrated circuit having an internal ROM 42 (read-only-memory) which is programmed, as set forth below, and a memory 43, upon which digital data may be entered, read and erased.

The program of microcontroller 37 is as follows: After electrodes 21–23 are secured in electrical contact with the skin of the patient, the device, automatically, will then establish a pre-treatment baseline reference by obtaining 2–5, preferably 3, sequential power levels. Alternatively, the user will push a button 44 labeled "Baseline" on the EEG device. The patient's brain waves for 3 spaced intervals of 1-second duration, are obtained and stored in the memory 43.

Preferably the microcontroller 37 is programmed to set the baseline level by storing and comparing a set of 50-200 integrated voltage periods using one-second periods. When 3 consecutive periods, each of 1-second duration, are within 10% of each other, their average value is taken as the baseline and the baseline acquisition halts. The baseline value is not itself used as the reference. Instead, a predetermined percentage of the baseline value is the reference, that percentage being in the range 50-90%, and preferably 70%. The reference which is determined to be the termination of the induced seizure is 70% of the baseline. The integrated voltage, for example, over a 1-second period, is 200 microvolts so the the 70% reference value is set at 140 microvolts.

When an ECT treatment is halted, the timer 14 of the ECT device halts and the microncontroller 37 terminates the voltage. The microcontroller 37, under its program, and under control of its internal clock, will count a predetermined interval of 2-10 seconds, preferably 5 seconds. This interval permits the electrical activity at the electrodes to dissipate and the seizure to be effected. At the end of the 5-second interval the EEG amplifier will be enabled, by microcontroller 37, via line 47, to detect the brain wave activity of the patient. The amplified brain waves, in integrated 1-second periods forming integrated voltages, are compared by microcontroller 37. When the reference level, for example, 70% of the baseline, is met, the microcomputer sends signals to a 4-digit LED (light-emitting diode) display 39 on line 38 and also a print command, on line 40, to the thermal printer 41, if the apparatus has a printer.

The LED display 39 and the thermal printer 41 both show the elapsed time from the end of ECT treatment (halt of voltage to the ECT electrode) to the end of the seizure, as determined, for example, by reaching 70% of the baseline.

However, the reference level may not be reached within a predetermined time in the range of 20-120 seconds, preferably 60 seconds, programmed into and clocked by microcontroller 37. In that event, according to the standard set by the predetermined reference level, it is automatically determined that a seizure has not occurred. The microcomputer signals the lack of seizure to LED display 39 which shows, for example, "00:00", and to the thermal printer 41, which prints, for example, "no seizure". In that event, the physician has the option to try another ECT treatment. He may then deliver another ECT electrical stimulus by triggering a treatment switch on the ECT device in order to deliver an electrical stimulus of selected duration.

If three consecutive prestimulus samples of electronically processed EEG signal (e.g., wide-band mean integrated voltage) are not within the selected range (e.g., 10% of each other) within a specified period, for example, 1 minute, of EEG sampling, the sampling procedure terminates. The operator is then informed, by LED display 39 and thermal printer 41, that the procedure must be repeated. For example, the LED display may read "99:99" and the printer 41 print out "baseline readings must be repeated".

The integrated voltage measured after the stimulus has terminated may fail to exceed the baseline voltage (prestimulus value) by a selected percentage, in the range of 10-50% and preferably 25%. The operator is then signaled on the LED display (for example, "00:01") and a printed record is made of the probability that evidence of a seizure is absent.

We claim:

1. A method in electroconvulsive therapy ECT to monitor the termination of an induced seizure in a patient, the method including the steps of:
    employing an ECT device, removably securing a plurality of electrodes on the head of the patient and applying electricity through the electrodes in an electroconvulsive therapy session to induce seizure, and
    detecting the electrical brain waves of the patient in an electroenocephalographic EEG device by amplifying the brain waves detected by at least one electrode removably secured to the head of the patient; establishing and storing in system memory a baseline reference of a brain wave parameter, detecting the patient brain waves to commence the monitoring of the termination of the seizure in the range of 1-30 seconds after ceasing the said application to induce seizure, automatically determining the termination of seizure as determined by the monitored brain wave parameter declining to the said established reference, displaying said termination of seizure, and
    including the step of measuring and displaying the elapsed time from the commencement of said monitoring until the said termination of seizure.

2. A method in electroconvulsive therapy as in claim 1 and displaying the lack of a seizure by failure to reach said reference within a selected time period.

3. A method in electroconvulsive therapy as in claim 1 wherein the parameter is integrated voltage over a selected time period in the range of 0.5-3 seconds.

4. A method in electroconvulsive therapy as in claim 3 wherein the selected period is about one second.

5. A method in electroconvulsive therapy as in claim 1 wherein said displaying of the elapsed time uses an LED time display.

6. A method in electroconvulsive therapy as in claim 1 wherein two detecting EEG electrodes are applied to the head of the patient on opposite sides of the head.

7. A method in electroconvulsive therapy as in claim 1 including the step of establishing the reference prior to said ECT therapy by measuring said parameter during at least two selected time periods, during which said periods the parameter is within a selected percentage of one period compared to another period, and averaging said parameter over said periods.

8. A system for electroconvulsive therapy ECT to monitor the termination of an induced seizure in a patient, the system including:
    an ECT device including a plurality of electrodes removably securable on the head of the patient and means for applying electricity through the electrodes in an electroconvulsive therapy session to induce seizure, and
    an electroencephalograph EEG means to detect electrical brain waves of the patient including means to amplify the brain waves and connected thereto, at least one electrode adapted to be removably secured to the head of the patient; system memory means to establish and store in system memory a baseline reference of a brain wave parameter, timer means to commence monitoring of brain waves for the termination of the seizure in the range of 1-30 seconds after ceasing the said application to induce seizure, measurement means for automatically measuring the termination of seizure as determined by the decline of the monitored brain wave parameter to the said baseline reference, display means to display said termination of seizure, an elapsed time means for measuring the time from said commencement of monitoring until the brain wave parameter decreases to said baseline reference, and display means for displaying said elapsed time.

9. A system for electroconvulsive therapy as in claim 8 wherein the ECT device, EEG means and the display means are in one electrically integrated system.

10. A system for electroconvulsive therapy as in claim 8 and means for determining and displaying the lack of a seizure by failure to reach said established reference within a selected time period.

11. A system in electroconvulsive therapy as in claim 10 wherein the selected period is about one second.

12. A system in electroconvulsive therapy as in claim 8 wherein the parameter is integrated voltage over a selected time period in the range of 0.5–3 seconds.

13. A system in electroconvulsive therapy as in claim 8 wherein the display means is an LED time display.

* * * * *